(12) United States Patent
Van Tilborg

(10) Patent No.: US 9,284,250 B2
(45) Date of Patent: Mar. 15, 2016

(54) 4-HYDROXY-2-METHYL-5-(PROPAN-2-YLIDENE)CYCLOHEX-3-ENECARBALDEHYDE FOR THE PREVENTION AND TREATMENT OF A COGNITIVE, NEURODEGENERATIVE OR NEURONAL DISEASE

(71) Applicant: CESA ALLIANCE S.A., Strassen (LU)

(72) Inventor: Reiner Van Tilborg, Strassen (LU)

(73) Assignee: CESA ALLIANCE S.A., Strassen (LU)

( * ) Notice: Subject to any disclaimer, the term of this patent is extended or adjusted under 35 U.S.C. 154(b) by 0 days.

(21) Appl. No.: 14/758,343

(22) PCT Filed: Dec. 17, 2013

(86) PCT No.: PCT/EP2013/076936
§ 371 (c)(1),
(2) Date: Jun. 29, 2015

(87) PCT Pub. No.: WO2014/102090
PCT Pub. Date: Jul. 3, 2014

(65) Prior Publication Data
US 2015/0361020 A1    Dec. 17, 2015

(30) Foreign Application Priority Data
Dec. 31, 2012  (LU) .......................................... 92126

(51) Int. Cl.
| | | |
|---|---|---|
| *A01N 35/00* | (2006.01) | |
| *A61K 31/11* | (2006.01) | |
| *C07C 47/46* | (2006.01) | |
| *A61K 47/44* | (2006.01) | |
| *A61K 9/00* | (2006.01) | |

(52) U.S. Cl.
CPC ............... *C07C 47/46* (2013.01); *A61K 9/0095* (2013.01); *A61K 31/11* (2013.01); *A61K 47/44* (2013.01); *C07C 2101/16* (2013.01)

(58) Field of Classification Search
CPC ..... A61K 31/11; A61K 47/44; A61K 9/0095; C07C 2101/16; C07C 47/46
See application file for complete search history.

(56) References Cited

FOREIGN PATENT DOCUMENTS

WO        01/68576 A1    9/2001

OTHER PUBLICATIONS

International Search Report for PCT/EP2013/076936 dated Jan. 21, 2014.

*Primary Examiner* — Wu-Cheng Winston Shen
*Assistant Examiner* — Jean Cornet
(74) *Attorney, Agent, or Firm* — Dennemeyer & Associates, LLC.

(57) ABSTRACT

The present invention concerns a pharmaceutical compound having the Formula (1):

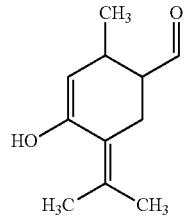

Formula (1)

or a pharmaceutically acceptable salt thereof,
for use in the prevention or treatment of a cognitive, neurodegenerative or neuronal disorder or disease such as the Alzheimer Disease,
a pharmaceutical composition and a method of preparing a pharmaceutical composition.

13 Claims, No Drawings

4-HYDROXY-2-METHYL-5-(PROPAN-2-YLIDENE)CYCLOHEX-3-ENECARBALDEHYDE FOR THE PREVENTION AND TREATMENT OF A COGNITIVE, NEURODEGENERATIVE OR NEURONAL DISEASE

The present invention relates to a chemical compound, a pharmaceutical compound for use as a medicament, a pharmaceutical compound for use in the treatment of a cognitive disorder or disease, a pharmaceutical composition, and a method of preparing a pharmaceutical composition. The compound of the present invention may be used in particular for treating the Alzheimer Disease.

DESCRIPTION—BACKGROUND

Alzheimer's disease (AD) is the most common form of dementia. Most often, it is diagnosed in people over 65 years of age, although the less-prevalent early-onset Alzheimer's can occur much earlier. In 2006, there were 26.6 million sufferers worldwide. Alzheimer's is predicted to affect 1 in 85 people globally by 2050. The earliest observable symptoms are often mistakenly thought to be 'age-related' concerns, or manifestations of stress. In the early stages, the most commonly recognised symptom is inability to acquire new memories, such as difficulty in recalling recently observed facts.

As the disease advances, gradually, bodily functions are lost, ultimately leading to death. Individual prognosis is difficult to assess, as the duration of the disease varies. AD develops for an indeterminate period of time before becoming fully apparent, and it can progress undiagnosed for years. The mean life expectancy following stage 2 diagnosis is approximately seven years. Fewer than three percent of individuals live more than fourteen years after diagnosis. In developed countries, AD is one of the most costly diseases to society.

A 2004 study tried to explain the causes of the AD and found that deposition of amyloid plaques does not correlate well with neuron loss. This observation supports the tau hypothesis, the idea that tau protein abnormalities initiate the disease cascade.

Another cause, on which most currently available drug therapies are based, is the cholinergic hypothesis, which proposes that AD is caused by reduced synthesis of the neurotransmitter acetylcholine. The cholinergic hypothesis has not maintained widespread support, largely because medications intended to treat acetylcholine deficiency have not been very effective. Other cholinergic effects have also been proposed, for example, initiation of large-scale aggregation of amyloid, leading to generalised neuroinflammation.

Four medications are currently approved by regulatory agencies such as the U.S. Food and Drug Administration (FDA) and the European Medicines Agency (EMA) to treat the cognitive manifestations of AD: three are acetylcholinesterase inhibitors and the other is memantine, an NMDA receptor antagonist. No drug has an indication for delaying or halting the progression of the disease. At present, there is no definitive evidence to support that any particular measure is effective in preventing AD.

The journal "Food chemistry" 116 (2009), pages 470 to 479, relates to the antioxidant, anticholinesterase and antimicrobial constituents from the essential oil and ethanol extract of *Salvia* potentillifolia.

The journal "Food chemistry" 108 (2008), pages 663 to 668, relates to the inhibitory effect of Turkish *Rosmarinus officinalis* L. on acetylcholinesterase and butyrylcholinesterase enzymes.

WO 01/68576 relates to dermatological compounds, i.e. novel monocyclic and bicyclic monoterpene diols that stimulate melanogenesis in mammalian skin, hair, wool or fur, and, are useful for treating or preventing various skin and proliferative disorders, neurodegenerative diseases, and diseases regulated by the nitric oxide/cyclic GMP/protein kinase G pathway.

WO 01/68576 can be regarded as representing the closest prior art because it discloses monoterpenes as pharmaceutically active compounds.

SUMMARY OF THE INVENTION

The chemical compound of the present invention, the pharmaceutical compound of the present invention, the pharmaceutical compound for use in the treatment of the Alzheimer disease, the pharmaceutical composition and the method of preparing the pharmaceutical composition are defined herein.

The technical effect of formula (1) of the present invention is to reduce the severity of the Alzheimer Disease from stage 6 to stage 4 or less.

The problem to be solved by the present invention is the provision of an alternative medicament for the prevention and/or treatment of cognitive, neurodegenerative and neuronal disorders or diseases, including the specific disorders or diseases of claim 4.

The proposed solution involves the use of the compound having the specific formula (1) or of a pharmaceutically acceptable salt thereof.

The chemical compound of claim 1 is novel and the skilled person would have no reason to modify the teaching in WO 01/68576 to thereby arrive at the subject-matter of the present invention. Doing so would involve an inventive step and skills beyond the ones that one would routinely expect from a person skilled in the art.

The Alzheimer disease course is divided into the following seven internationally recognized stages:

Stage 1: No impairment (normal function). The person does not experience any memory problems. An interview with a medical professional does not show any evidence of symptoms.

Stage 2: Very mild cognitive decline (may be normal age-related changes or earliest signs of Alzheimer's disease). The person may feel as if he or she is having memory lapses—forgetting familiar words or the location of everyday objects. But no symptoms can be detected during a medical examination or by friends, family or co-workers.

Stage 3: Mild cognitive decline (early-stage Alzheimer's can be diagnosed in some, but not all, individuals with these symptoms). Friends, family or co-workers begin to notice difficulties. During a detailed medical interview, doctors may be able to detect problems in memory or concentration. Common stage 3 difficulties include: noticeable problems coming up with the right word or name. Trouble remembering names when introduced to new people having noticeably greater difficulty performing tasks in social or work settings, forgetting material that one has just read losing or misplacing a valuable object, increasing trouble with planning or organizing. Lasts about 2 years.

Stage 4: Moderate cognitive decline (mild or early-stage Alzheimer's disease). At this point, a careful medical interview should be able to detect clear-cut problems in several areas: forgetfulness of recent events, impaired ability to perform challenging mental arithmetic (for example, counting backward from 100 by 7s), greater difficulty performing complex tasks, such as planning dinner for guests, paying bills or managing finances, forgetfulness about one's own personal history, becoming moody or withdrawn, especially in socially or mentally challenging situations. Lasts about 2 years.

Stage 5: Moderately severe cognitive decline (Moderate or mid-stage Alzheimer's disease). Gaps in memory and thinking are noticeable, and individuals begin to need help with day-to-day activities. At this stage, those with Alzheimer's may:

be unable to recall their own address or telephone number or the high school or college from which they graduated, become confused about where they are or what day it is, have trouble with less challenging mental arithmetic; such as counting backward from 40 by subtracting 4s or from 20 by 2s, need help choosing proper clothing for the season or the occasion, still remember significant details about themselves and their family, still require no assistance with eating or using the toilet. Lasts about 1 year.

Stage 6: Severe cognitive decline (moderately severe or mid-stage Alzheimer's disease). Memory continues to worsen, personality changes may take place and individuals need extensive help with daily activities. At this stage, individuals may: lose awareness of recent experiences as well as of their surroundings, remember their own name but have difficulty with their personal history, distinguish familiar and unfamiliar faces but have trouble remembering the name of a spouse or caregiver, need help dressing properly and may, without supervision, make mistakes such as putting pajamas over daytime clothes or shoes on the wrong feet, experience major changes in sleep patterns, sleeping during the day and becoming restless at night, need help handling details of toileting (for example, flushing the toilet, wiping or disposing of tissue properly), have increasingly frequent trouble controlling their bladder or bowels, experience major personality and behavioural changes, including suspiciousness and delusions (such as believing that their caregiver is an impostor) or compulsive, repetitive behaviour like hand-wringing or tissue shredding, tend to wander or become lost. Lasts about 1 year.

Stage 7: Very severe cognitive decline (Severe or late-stage Alzheimer's disease). In the final stage of this disease, individuals lose the ability to respond to their environment, to carry on a conversation and, eventually, to control movement. They may still say words or phrases. At this stage, individuals need help with much of their daily personal care, including eating or using the toilet. They may also lose the ability to smile, to sit without support and to hold their heads up. Reflexes become abnormal. Muscles grow rigid. Swallowing impaired. Lasts about 1 year.

DETAILED DESCRIPTION OF THE INVENTION

The present invention concerns a chemical compound having the specific Formula (1) and is defined in claim 1 and it concerns also a pharmaceutical compound or a pharmaceutically acceptable salt thereof, for use as a medicament, for use in medicine, having the same specific Formula (1) defined in claim 2:

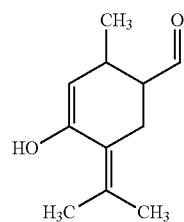

Formula (1)

Protection for the present invention is sought for the CIS isomer of formula (1) and also for the TRANS isomer of formula (1) (according to C=O and OH position in the carbon squelet plan where TRANS is the predominant isomer, about 70% to 99% of the compound of formula (1)). The CIS isomer is not the predominant isomer (about 1% to 30% of the compound of formula (1)) but it can nevertheless play an important role in the treatment of the disease:

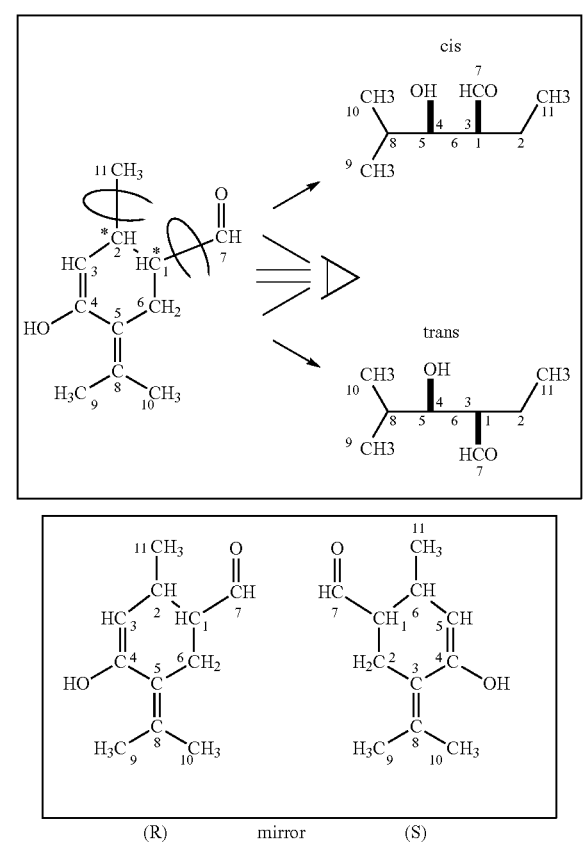

According to the Newman nomenclature the chiral carbon (1) leads to the two enantiomers (R) and (S) of formula (1) of the present invention.

The carbon atoms are numbered from 1 to 11 in the preceding mentioned representations of the (R) and (S) enantiomers.

The present invention concerns also a pharmaceutical compound having the specific Formula (1):

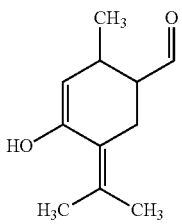

Formula (1)

or a pharmaceutically acceptable salt thereof,
for use in the prevention or treatment of a cognitive, neurodegenerative or neuronal disorder or disease, such as Alzheimer's disease and is defined in claim 3.

The cognitive, neurodegenerative or neuronal disorder or disease of the compound of the present invention is selected from:

chronic neurodegenerative conditions including dementias such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, [beta]-amyloid angiopathy and cerebral bleeding such as cerebral bleeding due to solitary cerebral amyloid angiopathy, prion infections, degenerative dementias, including dementias of mixed vascular and degenerative origin, frontotemporal dementia, pre-senile dementia, senile dementia, AIDS associated dementia, parkinsonian disorders such as Parkinson's disease (PD), subacute sclerosing panencephalitic parkinsonism, postencephalitic parkinsonism, pugilistic encephalitis, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis and neurotraumatic diseases such as acute stroke, epilepsy, promotion of functional recovery post stroke, ischaemia, brain injury, especially traumatic brain injury and neuroinflammation.

The pharmaceutical composition of the present invention comprises a pharmaceutically acceptable carrier and is defined in claim 5. The pharmaceutically acceptable carrier is a base oil selected from the group consisting in:

acai oil, almond oil, amaranth oil, apple seed oil, apricot oil, argan oil, artichoke oil, avocado oil, babassu oil, ben oil, blackcurrant seed oil, borage seed oil, borneo tallow nut oil, bottle gourd oil, buffalo gourd oil, butternut squash seed oil, cape chestnut oil, carob pod oil, carob seed pods oil, cashew oil, cassia oil, castor oil, cocklebur oil, cocoa butter, coconut oil, cohune oil, coriander seed oil, corn oil, cotton seed oil, dika oil, evening primrose oil, false flax oil, flax seed oil, grape seed oil, hazelnut oil, hemp oil, kapok seed oil, kenaf Seed oil, lallemantia oil, macadamia oil, marula oil, meadowfoam seed oil, mongongo nut oil (or manketti oil), mustard oil, nutmeg butter, oils from melon and gourd seeds, okra seed oil, olive oil, palm oil, papaya oil, peanut oil, pecan oil, pequi oil, perilla seed oil, pine nut oil, pine nut oil, pistachio oil, poppyseed oil, prune kernel oil, pumpkin seed oil, quinoa oil, radish oil, ramtil oil, rapeseed oil, rice bran oil, royle oil, sacha Inchi, safflower oil, salicornia oil, sesame oil, soybean oil, sunflower oil, tea seed oil, thistle oil, tigernut oil, tomato seed oil, tung oil, walnut oil, watermelon seed oil, wheat germ oil.

The base oil is a fatty acid selected from the group consisting in: lauric acid, myristic acid, palmitic acid, caprylic acid, capric acid, stearic acid, caprioc acid, oleic acid, linoleic acid, arachidic acid, behenic acid, lignoceric acid, palmitoeic acid, linoleic acid, sapienic acid, alpha-liolenic acid, arachidonic acid, erusapentaenoic acid, erucic acid, docosahexaunoic acid, cerotic acid.

The pharmaceutically acceptable carrier of the present invention is selected from the base oil as defined above or water or sugar or glycerol or a combination of the base oil as defined above and water and sugar and/or glycerol.

The pharmaceutical compound of the present invention to be taken daily by a human patient has an effective amount from 0.1 mg to 50 mg or from 1 mg to 40 mg or from 5 mg to 30 mg or from 7 mg to 25 mg or from 8 mg to 20 mg or from 9 mg to 15 mg per kilogram body weight.

The pharmaceutical compound of the present invention is administered orally or topically or parentally or by rectal route or by injection or by inhalation or by a patch or other delivery vehicles.

The pharmaceutical compound of the present invention is 4-hydroxy-2methyl-5-(propan-2-ylidene)cyclohex-3-ene-1-carbaldehyde.

The present invention concerns also a method of preparing pharmaceutical composition comprising the following steps:

blending the compound of formula (1) of the present invention at a temperature comprised preferably between 5° C. and 15° C. with a base oil at a rate of 5% to 20% by weight, preferably 10% to 15%, most preferably 11% to 14%;

obtention of a mixture;

wherein the compound of formula (1) of the present invention is present in the composition in an amount effective for treatment and prevention of a cognitive, neurodegenerative or neuronal disorder or disease selected from:

chronic neurodegenerative conditions including dementias such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, [beta]-amyloid angiopathy and cerebral bleeding such as cerebral bleeding due to solitary cerebral amyloid angiopathy, prion infections, degenerative dementias, including dementias of mixed vascular and degenerative origin, frontotemporal dementia, pre-senile dementia, senile dementia, parkinsonian disorders such as Parkinson's disease (PD), subacute sclerosing panencephalitic parkinsonism, postencephalitic parkinsonism, pugilistic encephalitis, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis and neurotraumatic diseases such as acute stroke, epilepsy, promotion of functional recovery post stroke, ischaemia, brain injury, especially traumatic brain injury and neuroinflammation.

The present disclosure also concerns a method for treating a subject suffering from a cognitive, neurodegenerative or neuronal disorder or disease, comprising the step of: administering a therapeutically effective amount of the pharmaceutical compound of formula (1) with or without any pharmaceutically acceptable carrier. The cognitive, neurodegenerative or neuronal disorder or disease being the Alzheimer's disease. The administration can be made either orally, or topically, or parentally, or by rectal route, or by injection, or by inhalation, or by a patch.

The present disclosure concerns a method for treating a subject suffering from a cognitive, neurodegenerative or neuronal disorder or disease, comprising the step of: administering a therapeutically effective amount of the pharmaceutical composition of the present invention. The cognitive, neurodegenerative or neuronal disorder or disease being the Alzheimer's disease. The administration can be made either orally, or topically, or parentally, or by rectal route, or by injection, or by inhalation, or by a patch.

The present disclosure concerns also a method for treatment and prevention of a cognitive, neurodegenerative or neuronal disorder or disease, said disorder or disease being the Alzheimer's disease, said method for treatment comprises the following step:

administering a therapeutically effective amount of the pharmaceutical compound of formula (1) together with an amount of a base oil as defined in the present invention either orally, or topically, or parentally, or by rectal route, or by injection, or by inhalation, or by a patch.

Any amount explicitly mentioned in the present invention concerning the compound of formula (1) and any amount concerning the base oil defined in the present invention can be used for the composition of the present invention, for the method of preparing pharmaceutical composition of the present invention and in the method for treatment and prevention of a cognitive, neurodegenerative or neuronal disorder or disease. Any technical feature mentioned in the present disclosure applies to the pharmaceutical compound of formula (1) of the present invention, to the composition of the present invention, to the method of preparing pharmaceutical composition of the present invention but also to the method for treatment and prevention of a cognitive, neurodegenerative or neuronal disorder or disease herewith disclosed.

Method of Manufacture and Galenics:

The purity of the components preferably has to be ≥99% and this is verified before the formulation process by gas chromatography/mass spectrometry.

The preferred temperature of manufacturing and storage of the composition is between 5 and 15 degrees Celcius.

The compound of the present invention can be blended to a pharmaceutically acceptable carrier to form a mixture. Depending on the type of application, the ratio between the composition of the present invention and the pharmaceutically acceptable carrier can range from 1% to 90%, from 10% to 80%, from 20% to 70%, from 30% to 60%, from 40% to 50%, where 20% is the most common ratio used for practical medical applications.

The mixture can then be further processed and integrated in capsules, gels, gelules, sprays, aerosols, suppositories or other drug delivery vehicles.

The method for manufacturing the composition of the present invention comprises the following steps:

blending the compound of formula (1) of the present invention at a temperature comprised preferably between 5 and 15° C. with a base oil at a rate of 5% to 20% by weight, preferably 10% to 15%, most preferably 11% to 14%. Other working ranges are 5% to 15% by weight, 5% to 14% by weight, 5% to 10% by weight, 5% to 11% by weight, 10% to 20% by weight, 10% to 15% by weight, 10% to 14% by weight, 10% to 11% by weight, 11% to 15% by weight, 12% to 13% by weight.

obtention of a mixture.

Synthesis:

The compound of the present invention (named RVT:A7), including salts thereof, can be prepared using known organic synthesis techniques and can be synthesized according to any of numerous possible synthesis routes.

The person skilled in the art would know how to manufacture the compound of the present invention.

The experimental manufacturing example, which follows, is illustrative and does not restrict the scope of the invention:

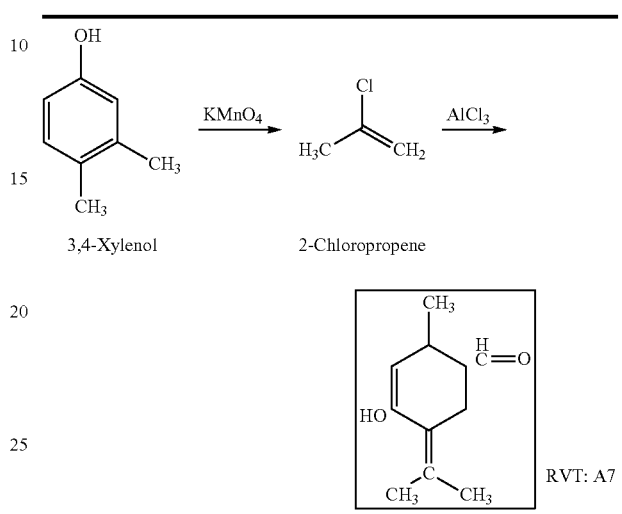

3,4-Xylenol    2-Chloropropene

RVT: A7

| Reactives | Reference | Quantity | Price (EUR) |
|---|---|---|---|
| benzylic alcohol | 305197 | | |
| 3,4 xylenol | W359602 | 250 g | 57 |
| 2-chloropropen | 254355 | 5 g | 102.5 |
| Ethanol 95% | 270660010 | | |
| Ether 5% | | | |
| $KMnO_4$ | 223468 | 25 g | 25.1 |
| $AlCl_3$ | 563919 | 5 g | 121.5 |
| PBS 10 X | D1408 | 6 × 500 ml | 148 |
| Tablets PBS | P4417 | 100 TAB | 103 |
| Glycerol | G5516 | 1 liter | 124 |
| Oil | other | 0.75 liter | 1 |

| A7: primer reaction | Reaction 44.4 ml final volume |
|---|---|
| Ethanol 95% ether 5% + 3,4 xylenol | 10 ml + 300 mg |
| $KMnO_4$ | 12.5 uL |
| 2-chloropropen + $AlCl_3$ | 1.5 ml + 8.4 mg |
| PBS 1X | qsp 40 ml |
| Glycerol | 4.4 ml |

| A7: 5 liters | Reaction 5 liters final volume |
|---|---|
| benzylic alcohol | 200 ml |
| A7 44 | 44 ml |
| PBS 1X | qsp 5 liters |
| oil | 0.75 liter |

Reaction in a Final Volume of 44.4 ml:

dissolve a quantity of 3,4 xylenol into an ethanol volume of 95%, ether 5% so that the xylenol is at 1M. PH control.

add a volume of $KMnO_4$/0.2 M so that its final concentration is 0.5 mM and incubate at TR during 15 minutes. PH control.

Add an equal volume of 2-chloropropen and $AlCl_3$ and incubate 5 minutes at 30° C.

Add a mixture of PBS and glycerol so that obtaining a final volume of 44 ml. Measuring the PH, putting parafilm and the tube is conserved at −20° C.

EXAMPLES

Experimental Data 1

Patient JH01

A 78 year old stage 6 Alzheimer confirmed patient (JH01) was diagnosed with Alzheimer's disease. The different stages of the AD are defined in the first pages of the present patent application. The patient was tested using the internationally recognized mini-mental state examination (MMSE) or Folstein test, a brief 30-point questionnaire test that is used to screen for cognitive impairment. The patient had a declining Mini-Mental State Examination (MMSE) score of 2 out of 30 at the beginning of the study (day 0).

The patient was given over 6 months 3 times a day 500 mg of a mixture of 80% by weight of Olive oil with 20% by weight of the compound of formula (1) of the present invention.

After one month, the care takers started to notice a general improved mental state of the patient.

After two months, the patient started to try to dress himself and started to ask about lunch and dinner times, which he never did in the past.

After three months, the patient could hold very small conversations with the care takers that made sense. He started to refer to certain events of the past.

After three months, a new MMSE was taken. Although the score was still very low, 8 out of 30 the improvement was considerable.

After 6 months, the patient mental state had improved considerably. Although he could not answer obvious questions like which province he was, this could be due to the fact that these questions were never asked in the past and there was no direct reference to them as then patient lived for years in a rather isolated environment.

He could however answer direct questions to very short term events.

After 6 months, the MMSE questions on these short term issues improved considerably and the score reached 13 out of 30 (see Table 1). This indicates that the patient could function as good as patient in stage 4 or less.

The unexpected improvement in total points over 6 months was 11 points on a scale of 30, which shows a surprising and unexpected improvement.

TABLE 1

Mini-Mental State Examination (MMSE)
Instructions: Score one point for each correct respons with each question or activity Patient's Name: JH01
Date:

| | Maximum score | Base | 3 months | 6 months |
|---|---|---|---|---|
| Orientation Time | | | | |
| 1. What is the year | 1 | 0 | 0 | 0 |
| 2. What is the season | 1 | 0 | 0 | 0 |
| 3. What is the month | 1 | 0 | 0 | 0 |
| 4. What is the date | 1 | 0 | 0 | 0 |
| 5. Which day of the week is it | 1 | 0 | 0 | 0 |
| Orientation in Place | | | | |
| 1. In which province are we now | 1 | 0 | 0 | 0 |
| 2. In which town are we now | 1 | 0 | 1 | 1 |
| 3. Where are we now (hospital/home) | 1 | 0 | 1 | 1 |
| 4. In what street are we now | 1 | 0 | 0 | 0 |
| 5. On which floor/in which number are we now | 1 | 0 | 0 | 0 |
| Memory | | | | |
| The examiner names 3 unrelated objects (eg apple-key-table) clearly and slowly, then the instructor asks for the patient to name all 3 of them. The patient's response is used for scoring. The words can be repeated afterwords (max 5 times) until patients knows all 3 | 3 | 1 | 1 | 2 |
| Concentration | | | | |
| "I would like you to count backward from 100 by sevens." (93, 86, 79, 72, 65, . . .) Alternative: "Spell the word WORLD backwards." (D-L-R-O-W) Maximum time given: 1 minute and 5 calculation | 5 | 0 | 0 | 0 |
| Memory 2 | | | | |
| "Earlier I told you the names of three things. Can you tell me what those were?" | 3 | 0 | 0 | 1 |
| Language | | | | |
| Show the patient 2 simple objects, such as a wristwatch and a pen and ask the patient to name them | 2 | 1 | 2 | 2 |
| Language 2 | | | | |
| "Repeat the phrase: No ifs, ands or buts." | 1 | 0 | 1 | 1 |

TABLE 1-continued

Mini-Mental State Examination (MMSE)
Instructions: Score one point for each correct respons with each question or activity Patient's Name: JH01
Date:

| | Maximum score | Base | 3 months | 6 months |
|---|---|---|---|---|
| Language 3 | | | | |
| "Take the paper in your right hand, fold it in half and put it on the floor (The examiner gives the patient a piece of blank paper.) Language 4 | 3 | 0 | 0 | 3 |
| "Please read this and do what it says." (Written instructions is "Close your eyes.") Language 5 | 1 | 0 | 1 | 1 |
| "Make up a sentence about anything." (This sentence must contain a noun and a verb) Language 6 | 1 | 0 | 1 | 1 |
| "Please copy this picture."  All 10 angles must be present and two must intersect | 1 | 0 | 0 | 0 |
| Total Score | 30 | 2 | 8 | 13 |

Folstein M F, Folstein S E, McHugh P R: "Mini-mental state: A practical method for grading the cognitive state of patients for the clinician." J Psychiatr Res 1975; 12:189-198.

From Table 1 it is apparent that the unexpected and surprising effect is that the patient gained 11 points 6 months after having taken 3 times a day the pharmaceutical composition of the present invention.

Experimental Data 2

Patient AA7-003

A 79 year old, stage 6 Alzheimer confirmed patient was administered 200 mg of the compound of formula (1) of the present invention mixed with 800 mg olive oil 3 times a day over a period of 6 months. The different stages are defined in the first pages of the present patent application.

The patient was tested using the internationally recognized mini-mental state examination (MMSE) or Folstein test, a brief 30-point questionnaire test that is used to screen for cognitive impairment. It is commonly used in medicine to screen for dementia, such as Alzheimer's disease. It is also used to estimate the severity of cognitive impairment and to follow the course of cognitive changes in an individual over time, thus making it an effective way to document an individual's response to treatment at which he scored 6 out of 30 at the beginning of the study (day 0).

The care taker was also questioned and the observations recorded using the internationally recognized Barthel Index (see Table 3), which consists of 10 items that measure a person's daily functioning specifically the activities of daily living and mobility. The items include feeding, moving from wheelchair to bed and return, grooming, transferring to and from a toilet, bathing, walking on level surface, going up and down stairs, dressing, continence of bowels and bladder.

The assessment can be used to determine a baseline level of functioning and can be used to monitor improvement in activities of daily living over time. The items are weighted according to a scheme developed by the authors. The person receives a score based on whether they have received help while doing the task. The scores for each of the items are summed to create a total score. The higher the score the more "independent" the person. Independence means that the person needs no assistance at any part of the task. If a person does about 50% independently then the "middle" score would apply.

The patient scored 50 out of 100 at the base line (see Table 3).

During the treatment the patient gradually regained cognitive ability and his daily functioning improved as well.

The patient experienced several periods of anxiety, which are contributed to the confusion, linked to the awakening of his cognitive abilities. The patient was given a controlled treatment of natural tranquilizers. After 3 months the periods of anxiety subsided indicating that he passed the critical reversal of the transition of stage 6 to stage 5.

After 6 months the Mini mental state examination (MMSE) score had increased with 9 points giving him a score of 15 out of 30 (see Table 2), a score that is close to the score of a 5-6 stage patient. This shows a surprising and unexpected improvement.

The Barthel Index of the same patient also increased considerably: 50 points (see Table 3). This also shows a surprising and unexpected improvement These experimental data indicate that the patient could function as good as a patient in stage 4 or less.

TABLE 2

Mini-Mental State Examination (MMSE)
Instructions: Score one point for each correct respons within each question or activity Patient: Observational Study AA7- Test Subject AA7-03

| | Max score | Base | 6 Months | +/− |
|---|---|---|---|---|
| Orientation Time | | | | |
| 1. What is the year | 1 | 0 | 0 | 0 |
| 2. What is the season | 1 | 0 | 0 | 0 |
| 3. What is the month | 1 | 0 | 0 | 0 |
| 4. What is the date | 1 | 0 | 0 | 0 |
| 5. Which day of the week is it | 1 | 0 | 0 | 0 |
| Orientation in Place | | | | |
| 1. In which province are we now | 1 | 0 | 0 | 0 |
| 2. In which town are we now | 1 | 1 | 1 | 0 |
| 3. Where are we now (hospital/home) | 1 | 1 | 1 | 0 |
| 4. In what street are we now | 1 | 0 | 1 | 1 |
| 5. On which floor/in which number are we now | 1 | 0 | 0 | 0 |
| Memory | | | | |
| The examiner names 3 unrelated objects (eg apple-key-table) clearly and slowly, then the instructor asks for the patient to name all 3 of them. The patient's response is used for scoring. The words can be repeated afterwords (max 5 times) until patients knows all 3 | 3 | 1 | 2 | 1 |
| Concentration | | | | |
| "I would like you to count backward from 100 by sevens." (93, 86, 79, 72, 65, . . .) Alternative: "Spell the word WORLD backwards." (D-L-R-O-W) Maximum time given: 1 minute and 5 calculations | 5 | 0 | 1 | 1 |
| Memory 2 | | | | |
| "Earlier I told you the names of three things. Can you tell me what those were?" | 3 | 0 | 1 | 1 |
| Language | | | | |
| Show the patient 2 simple objects, such as a wristwatch and a pen and ask the patient to name them | 2 | 2 | 2 | 0 |
| Language 2 | | | | |
| "Repeat the phrase: No if, ands or buts." | 1 | 0 | 1 | 1 |
| Language 3 | | | | |
| "Take the paper in your right hand, fold it in half and put it on the floor (The examiner gives the patient a piece of blank paper.) | 3 | 0 | 3 | 3 |
| Language 4 | | | | |
| "Please read this and do what it says." (Written instruction is "Close your eyes.") | 1 | 0 | 1 | 1 |
| Language 5 | | | | |
| "Make up a sentence about anything." (This sentence must contain a noun and a verb) | 1 | 1 | 1 | 0 |
| Language 6 | | | | |
| "Please copy this picture." All 10 angles must be present and two must intersect  | 1 | 0 | 0 | 0 |
| Total Score | 30 | 6 | 15 | 9 |

From Table 2 it is apparent that the unexpected and surprising effect is that the patient gained 9 points 6 months after having taken the pharmaceutical composition of the present invention.

TABLE 3

The Barthel Index
Instructions: score 0, 5, 10 or 15 points depending on patients abilities

| Patient's Name Observational Study AA7-Test Subject AA7-03 | Max score | Base | 6 Month | +/- |
|---|---|---|---|---|
| 1. Feeding | | | | |
| Independent | 10 | 5 | 10 | 5 |
| Needs help cutting, spreading butter, etc., or requires modified diet | 5 | | | |
| Unable | 0 | | | |
| 2. Bathing | | | | |
| Independent (or in shower) | 5 | 0 | 5 | 5 |
| Dependent | 0 | | | |
| 3. Grooming | | | | |
| Independent face/hair/teeth/shaving (implements provided) | 5 | 0 | 5 | 5 |
| Needs help with personal care | 0 | | | |
| 4. Dressing | | | | |
| Independent (includes buttons, zips, laces, etc.) | 10 | 5 | 10 | 5 |
| Needs help but can do about half unaided | 5 | | | |
| Dependent | 0 | | | |
| 5. Bowels | | | | |
| Continent | 10 | 5 | 10 | 5 |
| Occasional accident | 5 | | | |
| Incontinent (or needs to be given enemas) | 0 | | | |
| 6. Bladder | | | | |
| Continent | 10 | 5 | 10 | 5 |
| Occasional accident | 5 | | | |
| Incontinent, or cathetherized and unable to manage alone | 0 | | | |
| 7. Toilet use | | | | |
| Independent (on and off, dressing, wiping) | 10 | 5 | 10 | 5 |
| Needs some help but can do something alone | 5 | | | |
| Dependent | 0 | | | |
| 8. Transfers | | | | |
| Independent | 15 | 10 | 15 | 5 |
| Minor help (verbal or physical) | 10 | | | |
| Major help (one or two people, physical), can sit | 5 | | | |
| Unable, no sitting balance | 0 | | | |
| 9. Mobility | | | | |
| Independent (but may use any aid, eg stick) > 50 meters | 15 | 10 | 15 | 5 |
| Walks with help of one person (verbal or physical) > 50 meters | 10 | | | |
| Wheelchair dependent including corners, > 50 meters | 5 | | | |
| Immobile or < 50 meters | 0 | | | |
| 10. Stairs | | | | |
| Independent | 10 | 5 | 10 | 5 |
| Needs help (verbal, physical, carrying aid) | 5 | | | |
| Unable | 0 | | | |
| Total Score | 0-100 | 50 | 100 | 50 |

From Table 3 it is apparent that the unexpected and surprising effect is that the patient gained 50 points 6 months after having taken the pharmaceutical composition of the present invention.

The invention claimed is:

1. A compound of the Formula (1):

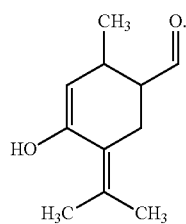

Formula (1)

2. A pharmaceutical composition comprising an effective amount of a compound of the Formula (1):

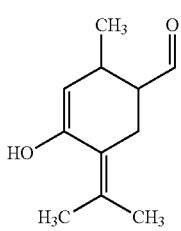

Formula (1)

or a pharmaceutically acceptable salt thereof and a pharmaceutically acceptable carrier.

3. The pharmaceutical composition of claim 2, wherein the pharmaceutically acceptable carrier is a base oil selected from the group consisting of:

acai oil, almond oil, amaranth oil, apple seed oil, apricot oil, argan oil, artichoke oil, avocado oil, babassu oil, ben oil, blackcurrant seed oil, borage seed oil, borneo tallow nut oil, bottle gourd oil, buffalo gourd oil, butternut squash seed oil, cape chestnut oil, carob pod oil, carob seed pods oil, cashew oil, cassia oil, castor oil, cocklebur oil, cocoa butter, coconut oil, cohune oil, coriander seed oil, corn oil, cotton seed oil, dika oil, evening primrose oil, false flax oil, flax seed oil, grape seed oil, hazelnut oil, hemp oil, kapok seed oil, kenaf Seed oil, lallemantia oil, macadamia oil, marula oil, meadowfoam seed oil, mongongo nut oil (or manketti oil), mustard oil, nutmeg butter, oils from melon and gourd seeds, okra seed oil, olive oil, palm oil, papaya oil, peanut oil, pecan oil, pequi oil, perilla seed oil, pine nut oil, pine nut oil, pistachio oil, poppyseed oil, prune kernel oil, pumpkin seed oil, quinoa oil, radish oil, ramtil oil, rapeseed oil, rice bran oil, royle oil, sacha Inchi, safflower oil, salicornia oil, sesame oil, soybean oil, sunflower oil, tea seed oil, thistle oil, tigernut oil, tomato seed oil, tung oil, walnut oil, watermelon seed oil, and wheat germ oil.

4. The pharmaceutical composition of claim 3, wherein the base oil comprising a fatty acid selected from the group consisting in of: lauric acid, myristic acid, palmitic acid, caprylic acid, capric acid, stearic acid, caprioc acid, oleic acid, linoleic acid, arachidic acid, behenic acid, lignoceric acid, palmitoeic acid, linoleic acid, sapienic acid, alpha-liolenic acid, arachidonic acid, erusapentaenoic acid, erucic acid, docosahexaunoic acid, and cerotic acid.

5. The pharmaceutical composition of claim 2, wherein the pharmaceutically acceptable carrier is selected from the base oil of claim 3 or water or sugar or glycerol or a combination of the base oil of claim 3 and water and sugar and/or glycerol.

6. A method of preparing the pharmaceutical composition of claim 2 comprising:
blending the compound of formula (1) of claim 2 with a base oil at a rate of 5% to 20% by weight at a temperature between 5° C. and 15° C.;
obtaining a mixture;
wherein said compound of formula (1) is present in the pharmaceutical composition in an amount effective for treatment of Alzheimer's disease.

7. A method of treating Alzheimer's disease in a human patient in need thereof comprising administering daily the pharmaceutical composition of claim 2 to said human.

8. The method of claim 7, wherein the effective amount of the compound of the formula (I) in the pharmaceutical composition is from 0.1 mg to 50 mg per kilogram body weight.

9. The method of claim 7, wherein the effective amount of the compound of the formula (I) in the pharmaceutical composition is from 1 mg to 40 mg per kilogram body weight.

10. The method of claim 7, wherein the effective amount of the compound of the formula (I) in the pharmaceutical composition is from 5 mg to 30 mg per kilogram body weight.

11. The method of claim 7, wherein the effective amount of the compound of the formula (I) in the pharmaceutical composition is from 7 mg to 25 mg per kilogram body weight.

12. The method of claim 7, wherein an effective amount of the compound of the formula (I) in the pharmaceutical composition is from 8 mg to 20 mg per kilogram body weight, or from 9 mg to 15 mg per kilogram body weight.

13. The method of claim 7, wherein the pharmaceutical composition is administered orally or topically or parentally or by rectal route or by intra dermal injection or by inhalation or by a patch.

* * * * *